United States Patent
Wandke et al.

(10) Patent No.: US 10,463,868 B2
(45) Date of Patent: Nov. 5, 2019

(54) DEVICE FOR TREATING A BODY SURFACE OF A LIVING BODY

(71) Applicant: CINOGY GMBH, Duderstadt (DE)

(72) Inventors: Dirk Wandke, Heilbad Heiligenstadt (DE); Leonhard Trutwig, Duderstadt (DE); Karl-Otto Storck, Duderstadt (DE); Mirko Hahnl, Berlingerode (DE); Frank Pallaske, Gersdorf (DE); Steffen Haertlein, Chemnitz (DE); Georg Daeschlein, Wandlitz OT Klosterfelde (DE)

(73) Assignee: CINOGY GMBH, Duderstadt (DE)

( * ) Notice: Subject to any disclaimer, the term of this patent is extended or adjusted under 35 U.S.C. 154(b) by 770 days.

(21) Appl. No.: 15/026,033

(22) PCT Filed: Nov. 6, 2014

(86) PCT No.: PCT/DE2014/000572
§ 371 (c)(1),
(2) Date: Mar. 30, 2016

(87) PCT Pub. No.: WO2015/070832
PCT Pub. Date: May 21, 2015

(65) Prior Publication Data
US 2016/0236002 A1 Aug. 18, 2016

(30) Foreign Application Priority Data
Nov. 15, 2013 (DE) .................. 10 2013 019 057

(51) Int. Cl.
*A61N 1/44* (2006.01)
*H05H 1/24* (2006.01)
*A61N 1/04* (2006.01)

(52) U.S. Cl.
CPC ............ *A61N 1/44* (2013.01); *A61N 1/0468* (2013.01); *H05H 1/2406* (2013.01); *H05H 2001/2418* (2013.01); *H05H 2277/11* (2013.01)

(58) Field of Classification Search
CPC ............... H05H 2001/2418; H05H 2001/2437
See application file for complete search history.

(56) References Cited

U.S. PATENT DOCUMENTS 6,136,278 A 10/2000 Eliasson et al.
7,569,359 B2 * 8/2009 McDonnell ............... A61L 2/28
422/504

(Continued)

FOREIGN PATENT DOCUMENTS

CA 2846684 A1 3/2013
DE 19739181 A1 3/1999

(Continued)

*Primary Examiner* — Kaitlyn E Smith
(74) *Attorney, Agent, or Firm* — W&C IP

(57) ABSTRACT

A device for treating a body surface of a living body by means of a dielectric barrier discharge plasma, with a planar, flexible dielectric (4) by which an electrode (1) attached to a high voltage source (3) is screened off from the body surface and which is suitable for placing on the body surface, functioning as counter-electrode, and is designed with a structured surface (7) which provides a gas space for the plasma discharge between dielectric (4) and body surface, which device permits the conduct of plasma treatment and the delivery of curative or healing substances without a change of the position of the device, by virtue of the fact that a layer (11) composed of a solid, open-pore matrix of a curative or healing material is arranged on the surface (7) of the dielectric (4).

10 Claims, 2 Drawing Sheets

(56) References Cited

U.S. PATENT DOCUMENTS

Figure 1:
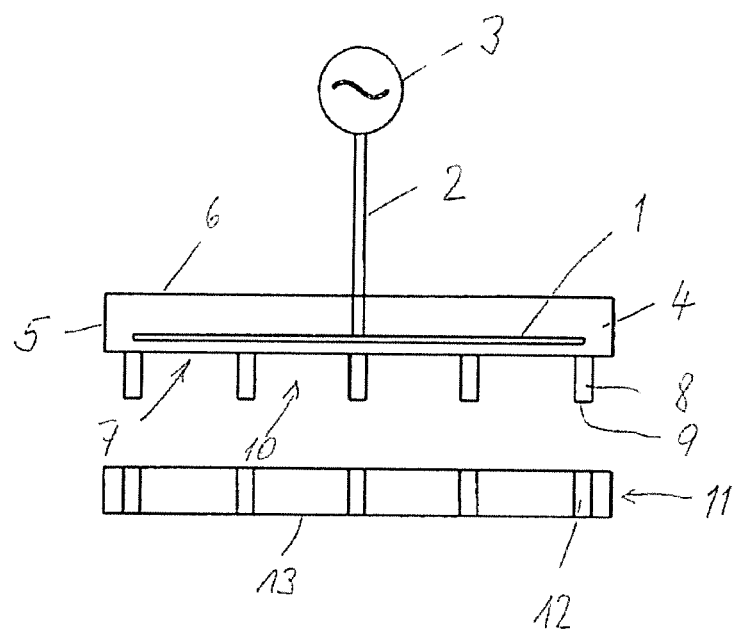

| | | | |
|---|---|---|---|
| 9,005,188 B2* | 4/2015 | Wandke | A61N 1/0408 606/32 |
| 2006/0083657 A1* | 4/2006 | McDonnell | A61L 2/28 422/504 |
| 2012/0107896 A1 | 5/2012 | Wandke et al. | |
| 2012/0259270 A1* | 10/2012 | Wandke | A61N 1/0408 604/23 |
| 2012/0271225 A1 | 10/2012 | Stieber et al. | |
| 2014/0188071 A1* | 7/2014 | Jacofsky | A61N 1/44 604/501 |
| 2015/0094647 A1* | 4/2015 | Kalghatgi | A61M 37/00 604/23 |
| 2016/0089545 A1* | 3/2016 | Juluri | A61K 9/0009 604/23 |
| 2017/0326347 A1* | 11/2017 | Kalghatgi | A61M 37/0015 |
| 2018/0295708 A1* | 10/2018 | Trutwig | A61L 2/14 |

FOREIGN PATENT DOCUMENTS

| | | |
|---|---|---|
| DE | 102008030913 A1 | 1/2010 |
| DE | 101008045830 A1 | 3/2010 |
| DE | 102009060627 A1 | 6/2011 |
| DE | 102011001416 A1 | 9/2012 |
| DE | 102011017249 A1 | 10/2012 |
| EP | 2170022 A1 | 3/2010 |
| EP | 2322232 A2 | 5/2011 |
| JP | 2012-503508 | 2/2012 |
| WO | 2010/034451 A1 | 4/2010 |
| WO | 2011023478 A1 | 3/2011 |
| WO | 2011076193 A1 | 6/2011 |
| WO | 2012/106735 A2 | 8/2012 |

* cited by examiner

DEVICE FOR TREATING A BODY SURFACE OF A LIVING BODY

The invention relates to a device for treating a body surface of a living body by means of a dielectric barrier discharge plasma, comprising a planar, flexible dielectric, which shields an electrode connected to a high-voltage source from the body surface and which is suitable for placement on the body surface acting as a counter electrode and which is embodied with a structured surface enabling a gas space for the plasma discharge between the dielectric and the body surface.

Such a device has been disclosed by DE 10 2009 060 627 A1. Here, the planar flexible dielectric has a larger embodiment in terms of area dimensions than the electrode connected to the high-voltage source such that the dielectric safely shields the electrode in the direction of the body surface, and so a destructive flashover onto the skin surface is reliably avoided. In this case, the electrode can also be embedded in the dielectric on all sides and merely lead out of the dielectric by means of a connection line. In the design of the known device, it is possible to place the dielectric in planar fashion directly onto the body surface. In order to enable the formation of the plasma discharge in the process, the surface of the dielectric pointing to the body surface is structured in such a way that gas spaces are formed between the dielectric and the body surface, in which the plasma discharge can take place.

In the case of a healthy body surface, the plasma treatment of the body surface may be carried out for cosmetic reasons, for example in order to disinfect the body surface and prepare it for a subsequent treatment with active ingredients, as result of which the uptake of the active ingredients through the skin is improved. Moreover, a plasma treatment of the body surface has proven its worth for promoting wound healing in particular, particularly in the case of chronic wounds. The plasma treatment has a strong antimicrobial effect, and so effects as a result of bacterial colonization, which interfere with the wound treatment, can be suppressed by means of the plasma treatment. Germs interfering with the wound healing include, in particular, *Staphylococcus aureus, Pseudomonas aeruginosa, E. coli* and other multi-resistant pathogens. Furthermore, the microcirculation in the tissue composite can be positively influenced by the action of the plasma.

In the conventional art, wound dressings are used for the wound treatment, in particular of chronic wounds, which wound dressings, in accordance with the principles of moist wound treatment, have sterile wound pads which are provided with various antiseptic active ingredients for reducing germs. Moreover, the wounds are rinsed in an antiseptic manner. In the case of deep layers, the wounds are additionally cleaned by means of surgical methods. These methods often only lead to an insufficient germ reduction, and so there continue to be risks of infection and risks of the germs spreading. In the case of strong colonization, in particular in the form of a bio-film, and if highly virulent pathogens occur, e.g. group A *Streptococcus*, the wound healing is delayed or even prevented as a result of infections. Effective methods based on the use of surgical techniques are all invasive, painful and require pain treatment and/or anesthetization.

By contrast, the invention is based on the object of specifying a device of the type set forth at the outset, by means of which the treatment of a body surface of a living body is possible in an improved manner.

In order to achieve this object, a device of the type set forth at the outset is, according to the invention, characterized in that a layer made of a solid, open-pore matrix of a curative or healing material is arranged on the surface of the dielectric.

The device according to the invention has an open-pore material on the surface of the dielectric, in which the dielectric barrier plasma discharge can form. Therefore, it is possible, firstly, to exploit the advantages of the plasma treatment of the body surface and, secondly, to keep the body surface in contact with the curative or healing material. Therefore, the contact with the curative or healing material need not be forfeited in order to carry out the plasma treatment, as would be required if a plasma treatment and a curative or healing treatment were to be carried out in succession. Particularly in the case of wound dressings, removing the wound dressing for carrying out the plasma treatment would be very bothersome in some circumstances.

Therefore, the device according to the invention enables the combined treatment of the body surface in the form of a plasma treatment, which is preferably carried out a number of times, and a treatment with a curative or healing material.

The layer made of the curative or healing material can be embodied as a separate layer with a surface that is complementary to the structured surface of the dielectric. This is advantageous because this avoids the creation of air gaps, and so there is a uniform plasma formation within the layer.

The layer is preferably embodied in such a way that it is bendable with the dielectric. In this way, the advantage of the flexible electrode arrangement, which can be placed with the dielectric on irregularly formed body parts as well, is maintained.

Like in the electrode arrangement known from DE 10 2009 060 627 A1, the structuring of the surface of the dielectric also can be formed from protruding bumps for the device according to the invention. The bumps preferably have a free planar end side for placement on the body surface.

In a particularly preferred embodiment, the layer consists of material that is resorbable by the body. The layer consists of collagen in a preferred embodiment such that the layer is resorbed by the body over a period of the order of a few days. An advantage offered by the device according to the invention is that a plasma treatment of the body surface still is possible, even after the resorption of the layer made of the curative or healing material, in particular collagen. Therefore, in the case of treating a chronic wound, a plasma treatment can be carried out, optionally repeatedly as well, without modifying the arrangement, even after the healing resorption of the collagen.

The production of a solid, flexible matrix made of collagen, as can be used in the device according to the invention, is known, in principle, from EP 2 322 232 A2. Therefore, an explanation in relation to the production of this layer can be dispensed with here.

It is known that certain layers made of healing or curative material can also be grown onto a plastic carrier, as a result of which the layer is immediately securely connected to the plastic carrier. Thus, the layer need not be produced as a separate layer in this case; instead, it can grow onto the structured surface of the dielectric. This is advantageous, particularly for a collagen layer. In this case, the grown layer automatically is formed in a manner complementary to the structuring of the surface of the dielectric.

The combination, according to the invention, of the device for the plasma treatment with a structured dielectric surface and the application of a layer of healing or curative material which, in particular, is completely resorbable by the body opens up numerous advantageous treatment options in the field of cosmetics and, in particular, medicine. Significant successes can be obtained in the healing of wounds which otherwise heal badly or not all, particularly in combination with a collagen layer.

The invention is intended to be explained in more detail below on the basis of an exemplary embodiment depicted in the drawing.

Figure 2:
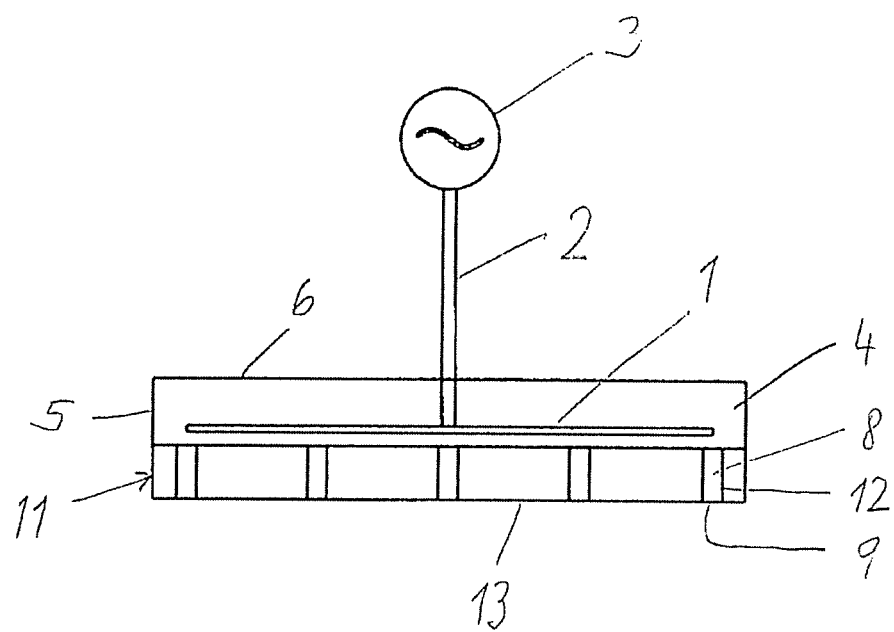

In detail:

FIG. 1 shows a schematic illustration of a device comprising a dielectric with a structured surface and a separately created layer, the surface of which is embodied in a manner complementary to the surface of the dielectric; and FIG. 2 shows the arrangement from FIG. 1 in the assembled state suitable for the application.

From the schematic illustration in the drawing, it is possible to identify a planar, flexible electrode 1, which is connected to a high-voltage source 3 by means of a suitable line 2. In the depicted exemplary embodiment, the high-voltage source supplies AC current.

The electrode is embedded in a planar dielectric 4 and therefore completely shielded from the surroundings. The planar dielectric therefore has narrow sides 5 and large side surfaces in the form of a rear side 6 and a treatment side 7 opposite thereto. On the treatment side 7, there are bumps 8 projecting from the cuboid body of the dielectric 4, which bumps have a cylindrical embodiment in the depicted exemplary embodiment but can also have any other form. The bumps 8 preferably have a cylindrical embodiment and the same height such that free, planar end sides 9 are able to form a common resting surface on a body surface to be treated. Here, an interspace 10 level with the bumps 8 is formed between the bumps when the electrode arrangement is placed by means of the end faces 9 of the bumps on a body surface to be treated.

According to the invention, a layer 11 formed from an open-pore matrix made of a curative or healing material interacts with the electrode arrangement known to this extent from DE 10 2009 060 627 A1. Here, a layer which, as a carrier layer, is doped with curative or healing substances is also understood to be a curative or healing material.

The layer has an embodiment that is complementary to the surface of the electrode arrangement facing the body surface. Accordingly, the layer 11 fills the interspace 10 between the bumps 8 and has openings 12 which are complementary to the bumps 8 such that the layer 11 completes the dielectric 4 to form a planar electrode arrangement with a smooth contact side 13 for placement on the body surface in the assembled state, as is depicted in FIG. 2.

In the depicted exemplary embodiment, the thickness of the layer 11 corresponds to the length of the bumps 8. This is advantageous if the layer 11 consists of a material that is completely resorbable by the body. Hence, the layer disappears over the course of the application and the electrode arrangement, depicted separately in FIG. 1, remains on the body surface without the layer 11. When the thickness of the layer 11 corresponds to the length of the bumps 8, the end sides 9 of the bumps 8 are flush with the contact side 13; i.e., they already rest against the body surface when the layer 11 still is present in its entirety. Therefore, the position of the electrode arrangement does not change when material of the layer 11 is resorbed by the body.

However, it is also possible for the layer 11 to have a thicker embodiment than the length of the bumps 8 such that the layer 11 has corresponding cylindrical blind holes as openings 12 in the case of cylindrical bumps 8. This is particularly unproblematic if the material of the layer is not resorbed but only contains curative or healing constituents which migrate into the body surface. If the layer 11 consists of resorbable material, the distance between the dielectric 4 and the body surface will reduce when the layer 11 disappears as a result of resorption. Hence, in this case, it is necessary to ensure that the electrode arrangement is fastened to the body surface under a certain amount of pretension such that the dielectric 4 can follow in the direction of the body surface when the layer 11 is resorbed.

The material of the layer 11 is preferably a solid collagen matrix, which promotes wound healing and which is completely resorbable. The production of such a matrix is described in EP 2 322 232 A2, with reference being made thereto.

The dielectric 4 is preferably a castable plastic such that the bumps 8 can be formed in an integral manner onto the dielectric 4. However, it is also conceivable for the bumps 8 to be manufactured separately and connected to the dielectric 4. In this case, the bumps 8 can form a cohesive part of the dielectric 4 and can be connected with a counterpart to form the dielectric 4. Expediently, the electrode 1 is inserted between the two parts of the dielectric 4 in the case of such a two-part design.

Completely embedding the electrode 1 in the dielectric 4, as depicted in the drawing, is advantageous and, in particular, also allows the integral embodiment of the dielectric 4 with the bumps 8. However, use cases in which the dielectric 4 merely brings about the shielding of the electrode 1 in the direction of the treatment side 7 such that a flashover from the electrode 1 to the body surface is suppressed with certainty are also conceivable. Covering the electrode 1 toward the rear side 6 can optionally be dispensed with or insulation can be brought about in a different manner.

The illustrated bumps 8 are only one conceivable embodiment of the structuring of the treatment side 7 of the dielectric 4. Any type of structuring, for example in the form of parallel grooves, grid-shaped notches or the like, is possible in order to form an interspace 10 which is required for the plasma discharge. The layer 11 which has a complimentary embodiment to the surface of the dielectric 4 and which completely fills the interspace 10 forms channels between the dielectric 4 and the body surface due to the open pore property thereof, in which channels the dielectric barrier plasma discharge takes place between the electrode 1 and the body surface as a counter electrode. Hence, the plasma discharge is performed within the channels present in the material of the layer 11.

In this case, the structuring of the treatment side 7 of the dielectric need not follow a regular pattern either. All that is important is a statistically uniform distribution of the interspace 10 over the active surface on the treatment side 7 such that there is a uniform plasma formation over the treatment area.

The invention claimed is:

1. A device for treating a body surface of a living body by means of a dielectric barrier discharge plasma, comprising:
   an electrode connected to a high voltage source;
   a planar, flexible dielectric which shields the electrode connected to the high-voltage source from the body surface and which is suitable for placement on the body surface acting as a counter electrode, wherein the dielectric is embodied with a structured surface enabling a gas space for plasma discharge between the dielectric and the body surface; and a layer made of a solid, open-pore matrix of a curative or healing material arranged on the structured surface of the dielectric.

2. The device as claimed in claim 1, wherein the layer is embodied as a separate layer with a surface that is complementary to the structured surface of the dielectric.

3. The device as claimed in claim 1 wherein the layer is bendable with the dielectric.

4. The device as claimed in claim 1 wherein the structured surface of the dielectric is formed from protruding bumps.

5. The device as claimed in claim 4, wherein the bumps have a free planar end side for placement on the body surface.

6. The device as claimed in claim 4 wherein a thickness of the layer corresponds to a length of the protruding bumps.

7. The device as claimed in claim 1 the layer is resorbable by the body.

8. The device as claimed in claim 7, wherein the layer consists of collagen.

9. The device as claimed in claim 1 wherein the layer is formed as a coating of the dielectric.

10. The device as claimed in claim 1 wherein the layer is formed by growth on the dielectric.

\* \* \* \* \*